(12) United States Patent
Dinwiddie

(10) Patent No.: US 7,986,990 B2
(45) Date of Patent: Jul. 26, 2011

(54) SYSTEM AND METHOD FOR DETECTING EXTREMELY LOW FREQUENCY ELECTRIC FIELDS IN THE HUMAN BODY

(76) Inventor: John Dinwiddie, Cary, NC (US)

( * ) Notice: Subject to any disclaimer, the term of this patent is extended or adjusted under 35 U.S.C. 154(b) by 267 days.

(21) Appl. No.: 12/416,376

(22) Filed: Apr. 1, 2009

(65) Prior Publication Data
US 2010/0256508 A1 Oct. 7, 2010

(51) Int. Cl.
*A61B 5/04* (2006.01)
(52) U.S. Cl. .......................................... 600/509
(58) Field of Classification Search .............. 600/509, 600/300, 407, 500, 515, 547; 607/2, 50, 607/38
See application file for complete search history.

(56) References Cited

U.S. PATENT DOCUMENTS

| | | | |
|---|---|---|---|
| 3,971,034 A | 7/1976 | Bell, Jr. et al. | |
| 4,233,965 A | 11/1980 | Fairbanks | |
| 4,444,199 A | 4/1984 | Shafer | |
| 4,723,536 A | 2/1988 | Rauscher et al. | |
| 4,889,526 A * | 12/1989 | Rauscher et al. | 600/14 |
| 5,296,866 A | 3/1994 | Sutton | |
| 5,313,944 A | 5/1994 | Crowley et al. | |
| 5,444,373 A | 8/1995 | Johnson et al. | |
| 5,730,138 A | 3/1998 | Wang | |
| 6,102,846 A | 8/2000 | Patton et al. | |
| 6,361,501 B1 | 3/2002 | Amano et al. | |
| 6,442,420 B1 * | 8/2002 | Julu et al. | 600/509 |
| 6,537,229 B1 | 3/2003 | Wang | |
| 6,723,054 B1 | 4/2004 | Baruch et al. | |
| 6,858,000 B1 | 2/2005 | Schukin et al. | |
| 7,087,025 B2 | 8/2006 | Baruch | |
| 7,191,134 B2 | 3/2007 | Nunally | |
| 7,249,603 B2 | 7/2007 | El-Nokaly et al. | |
| 7,664,551 B2 * | 2/2010 | Cigaina | 607/40 |
| 2005/0203578 A1 | 9/2005 | Weiner et al. | |
| 2009/0156949 A1 * | 6/2009 | Hu et al. | 600/515 |

FOREIGN PATENT DOCUMENTS
EP 1287803 3/2003

OTHER PUBLICATIONS

Hsu, Tse Lin et al., "Organ-specific ligation-induced changes in harmonic components of the pulse spectrum and regional vasoconstrictor selectivity in Wistar rats," Experimental Physiology 2006, 91.1, pp. 163-170.
Lu, Wan-An, "Pulse Spectrum Analysis in Primary Hypertension Patients," Taipei City Medical Journal, vol. 3 No. 9, 2006, pp. 23-32.

(Continued)

*Primary Examiner* — George Manuel
*Assistant Examiner* — Robert N Wieland
(74) *Attorney, Agent, or Firm* — Coats & Bennett, P.L.L.C.

(57) ABSTRACT

A sensor, such as an antenna, detects an electrical sinoatrial signal produced by the human heart. A spectrum analyzer then processes the electrical sinoatrial signal to generate a frequency spectrum comprising a plurality of frequency components associated with different organs. A diagnostic unit then analyzes the frequency spectrum and compares the frequency spectrum to a standardized normal spectrum to determine the condition of the organs. In particular, the amplitude and the bandwidth of the frequency components may be compared to the standardized normal spectrum. The system monitors the relationship between the electromagnetic energy of the heart, organs, limbs, and the brain.

18 Claims, 6 Drawing Sheets

OTHER PUBLICATIONS

Lu, Wan-An, "Pulse-Spectrum Analysis in 205 Patients with Abnormal Liver Function Test," Taipei City Medical Journal, vol. 3, No. 3, 2006, pp. 47-54.

Lau, Elizabeth O.Y., et al. "Relationship between Wrist-pulse Characteristics and Body Conditions," 14th Engineering Mechanics Conference, May 2000, 6 pages, http://www.ce.utexas.edu/em2000/papers/Allench2.pdf.

Wei, Ching-Chuan et al., "Study on Circuit Model of Organ Resonance Theory," 5 pages, http://ace136.auto.fcu.edu.tw/~cslin/confer/2002/paper/d11.pdf.

"Memorandum Addressing Electric and Magnetic Field (EMF) Questions," Cape Wind Energy Project, Nantucket Sound, Aug. 2005, 17 pages, http://www.mms.gov/offshore/PDFs/CWFiles/141.pdf.

J. Lipkova and J. Cechak, "Human electromagnetic emission in the ELF band," Measurement Science Review, vol. 5, Sec. 2, 2005, pp. 29-32.

Y.C. Kuo, et al, "Harmonic Variations of Arterial Pulse during Dying Process of Rats," Papers from 23rd Annual International Conference of the IEEE Engineering in Medicine and Biology Society held in Istanbul, Turkey, Oct. 25-28, 2001, 4 pages.

C. J. Harland, et al., "Remote detection of human electroencephalograms using ultrahigh input impedance electric potential sensors," Applied Physics Letters, vol. 81, No. 17, Oct. 21, 2002, pp. 3284-3286.

* cited by examiner

SYSTEM AND METHOD FOR DETECTING EXTREMELY LOW FREQUENCY ELECTRIC FIELDS IN THE HUMAN BODY

TECHNICAL FIELD

The present invention relates generally to detecting and measuring the presence of disease in the human body. In particular, the present invention relates to detecting an electrical sinoatrial signal produced by the human heart and determining the condition of organs and limbs of the human body, based on the detected electrical sinoatrial signal.

BACKGROUND

Extremely low frequency (ELF) electromagnetic waves have frequencies between 1 and 30 Hz. ELF waves are found as a natural occurrence in the environment and in man-made electronic devices. Naturally occurring ELF waves resonant in a cavity formed by the earth's surface and the ionosphere. The conducting terrestrial surface of the earth and the conducting ionosphere separated by an insulating layer of air creates the earth-ionosphere cavity. The ELF resonance in the earth-ionosphere cavity is generally referred to as Schumann resonance and can be viewed as separate spectral peaks.

Many sensors used to measure Schumann resonances consist of two horizontal magnetic induction coils for measuring the north-south and east-west components of the magnetic field and a vertical electric dipole antenna for measuring the vertical component of the electric field. However, the ELF frequency range generally overlaps the vibration spectrum of the antenna, which induces unwanted noise voltage in the antenna. To stabilize the antenna, the length of the antenna is generally increased. For example, the vertical component of the electric field can be measured using a 36.5 meter vertical mast. Other antennas used to measure the ELF resonance include extremely large horizontal antennas, ball-over-plane configurations having an antenna height of approximately 1 meter, and spherical antennas mounted on a gimbaled mast approximately 10 meters above the ground.

Smaller entities, such as organs and limbs of the human body also produce ELF resonant cavities. Each organ and limb resonates in a different frequency. However, the antennas previously developed are too large for conveniently measuring ELF resonance in the human body.

SUMMARY

The present invention provides a system and method for detecting and measuring disease in organs and limbs of the human body. In one embodiment, the system comprises a sensor for sensing an electrical sinoatrial signal produced by a human heart, a spectrum analyzer for processing the electrical sinoatrial signal and generating a frequency spectrum based on the electrical sinoatrial signal, and a diagnostic unit for determining the condition of the organs by comparing the spectrum to a standardized normal spectrum associated with healthy organs. The frequency spectrum comprises a plurality of frequency components associated with different organs. The amplitude, bandwidth, and/or quality factor (Q) of the frequency components may be analyzed to determine the condition of the organs.

The present invention is not limited to the above summary of features and advantages. Indeed, those skilled in the art will recognize additional features and advantages upon reading the following detailed description, and upon viewing the accompanying drawings.

BRIEF DESCRIPTION OF THE DRAWINGS

A person skilled in the art will understand that the drawings described below are for illustration purposes only. The drawings are not intended to limit the scope of the present teachings in any way.

DETAILED DESCRIPTION

The present invention provides a system and method for detecting and measuring the presence of disease in the organs and limbs of the human body. In particular, the present invention detects an electrical sinoatrial signal (heartbeat) produced by the human heart and converts the signal into a frequency spectrum. The spectrum represents the ELF resonance of different organs and limbs of the human body. Based on the spectrum, a physician can determine whether organs and limbs associated with the acquired spectrum are healthy or diseased.

The sinoatrial node is the impulse generating tissue on the right atrium of the heart. The sinoatrial node generates electrical impulses that cause the heart to contract. Organs and limbs of the body are connected to sinoatrial node by human meridians, which are conductive pathways within the human body for conducting electromagnetic energy from the sinoatrial node to the organs and limbs. Human meridians are high conductance, low impedance, ELF transmission lines that function as a band-pass filter for electromagnetic energy in the ELF band between 0.1 and 40 hertz and transfer energy from the sinoatrial node to organs and limbs. The organs and limbs in the human body behave like spherical resonant cavities. The component frequencies of the electrical pulse are generated from the impedance of the organs and limbs of the body. Each organ and limb receives a specific frequency of electromagnetic energy generated by the sinoatrial node specifically for that organ or limb. If an organ or limb does not receive adequate energy, then that organ or limb becomes diseased. Healthy organs and limbs are reflected by a balanced distribution of the ELF energy within the body. Ailments in the body are reflected in the distribution of the ELF energy within the body, and can be diagnosed by analyzing the spectral content of the electrical sinoatrial signal.

Figure 1:
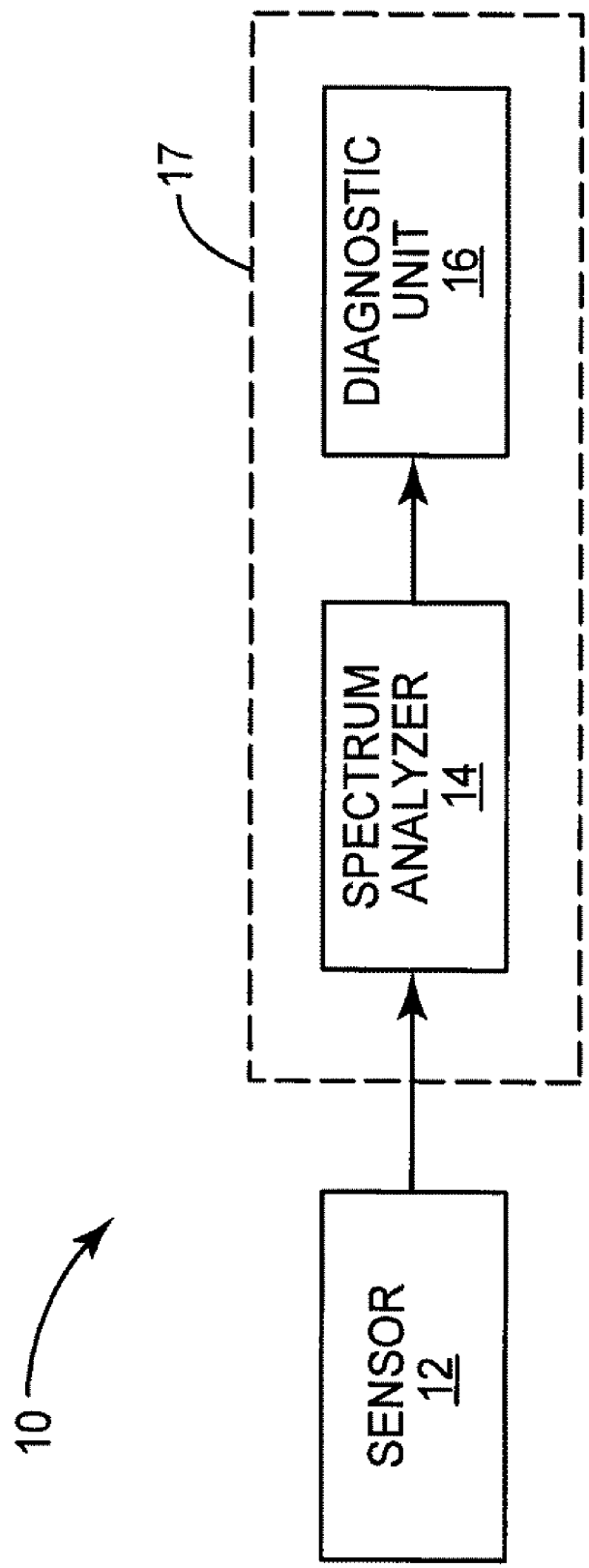
FIG. 1 is a block diagram illustrating a system for detecting an electrical sinoatrial signal and determining the conditions of the organs based on the detected signal configured according to one embodiment of the present invention.

As shown in FIG. 1, diagnostic system 10 detects an electrical sinoatrial signal representing ELF resonance in the human body and determines the conditions of organs and limbs in the human body based on the detected signal. System 10 includes sensor 12, spectrum analyzer 14, and diagnostic unit 16. Sensor 12 acquires the electrical sinoatrial signal produced by the human heart and is coupled to spectrum analyzer 14 which generates a frequency spectrum based on the acquired electrical sinoatrial signal. Each frequency component, or peak, in the spectrum is associated with the ELF electromagnetic resonance oscillating in resonant cavities produced by an organ or a limb in the human body. Diagnostic unit 16, coupled to spectrum analyzer 14, analyzes the frequency spectrum to determine if various organs or limbs are healthy or diseased. In one embodiment, diagnostic unit 16 compares the acquired frequency spectrum to a standardized normal spectrum associated with healthy organs to determine the relative health of organs and limbs. The spectrum analyzer 14 and diagnostic unit 16 can be implemented in software executed by a specially-programmed computer 17.

Figure 2:
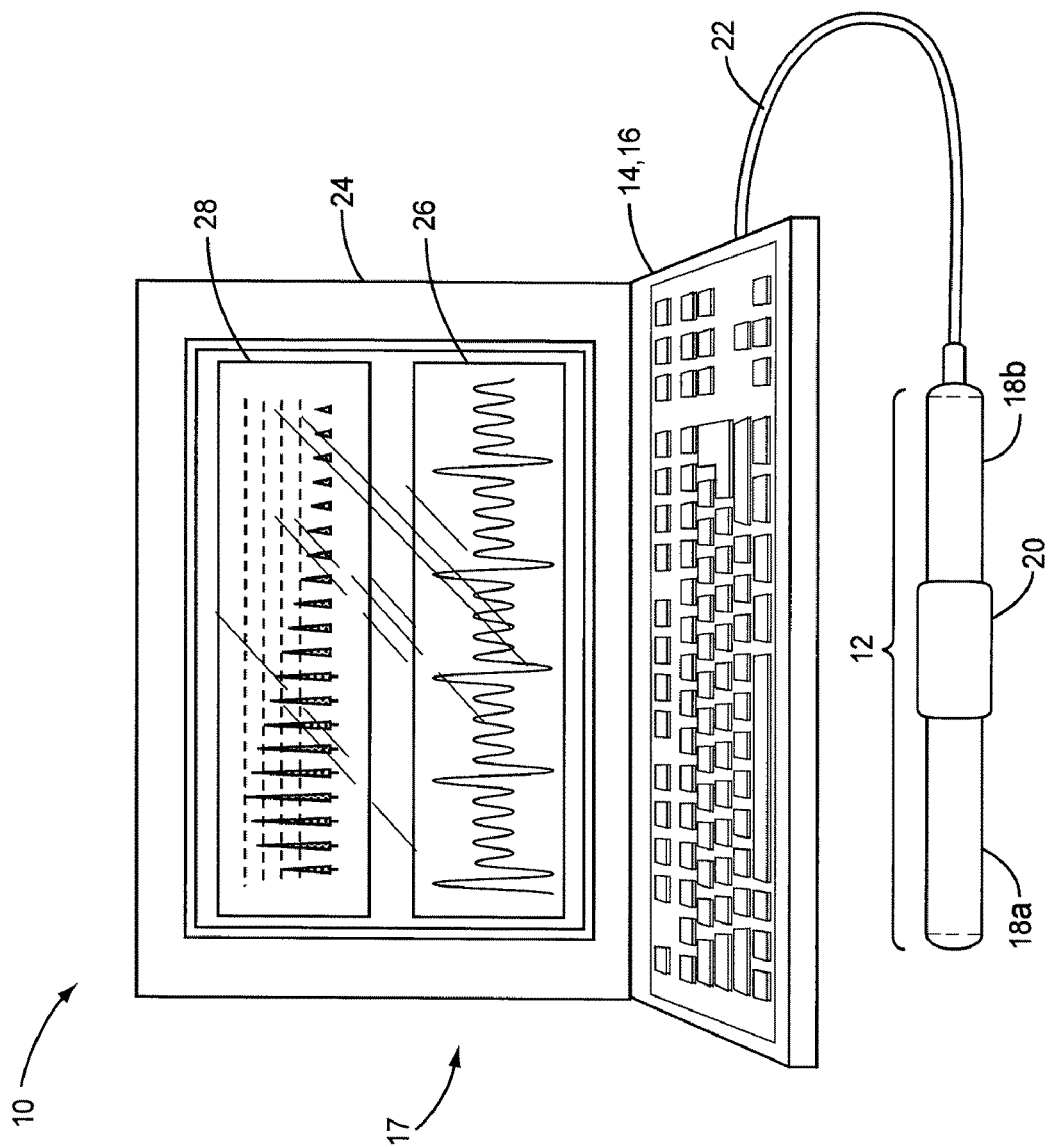
FIG. 2 illustrates in perspective view a diagnostic system configured according to one embodiment of the present invention.

A perspective view of the diagnostic system 10 configured according to one embodiment of the present invention is shown in FIG. 2. Sensor 12 receives electromagnetic resonance between 0.1 and 40 hertz which allows the antenna to receive signals in the ELF band produced by the sinoatrial node, that reflect the impedance of the organs and limbs in the human body. As shown in FIG. 2, sensor 12 comprises an electrically small, ELF electric field, dipole antenna having a capacitance of approximately 30 pF between first and second conductive elements 18a, 18b. In a preferred embodiment, conductive elements 18a, 18b are copper, silver or gold. Highly conductive metals, such as copper, silver, and gold provide a greater signal to noise ratio than metals with lower conductivity, such as aluminum and brass. In one embodiment, conductive elements 18a, 18b are copper with nickel plating coated over the copper and gold plating coated over the nickel plating to reduce oxidation on conductive elements 18a, 18b. In one embodiment, conductive elements 18a, 18b each have a length of approximately 6 inches and an outer diameter of approximately ¾ inches.

The first conductive element 18a is separated from the second conductive element 18b by an electrical insulator, such as air. In one embodiment, an air gap of approximately ½ inch separates conductive elements 18a, 18b. In addition, an insulating tube 20, made from a material such as PTFE (Teflon®) supports conductive elements 18a, 18b with respect to each other. In one embodiment, the insulating tube 20 is approximately 2-3 inches in length and has an outer diameter of approximately 1 inch. As discussed in more detail below in reference to FIG. 3, at least one of the conductive elements 18a, 18b of sensor 12 includes internal electrical circuitry that enables the sensor 12 to acquire an electrical sinoatrial signal produced by the human heart.

Sensor 12 is coupled to a computer 17 by a cable 22. The computer is programmed to function as a spectrum analyzer 14 and diagnostic unit 16. The spectrum analyzer 14 converts the signal acquired by sensor 12 into the frequency domain and generates a frequency spectrum 28 based on the acquired signal. One example of frequency spectrum 28 is shown in FIG. 2 on display 24 along with an example of an acquired electrical sinoatrial signal 26.

After the electrical sinoatrial signal 26 is converted into the frequency spectrum 28, a diagnostic unit 16 analyzes the frequency spectrum 28 to determine the relative condition of organs and limbs in the human body. As previously stated, diagnostic unit 16 may comprise a software program executed by the computer that compares the acquired frequency spectrum to a standardized normal frequency spectrum associated with healthy organs and limbs.

Figure 3:
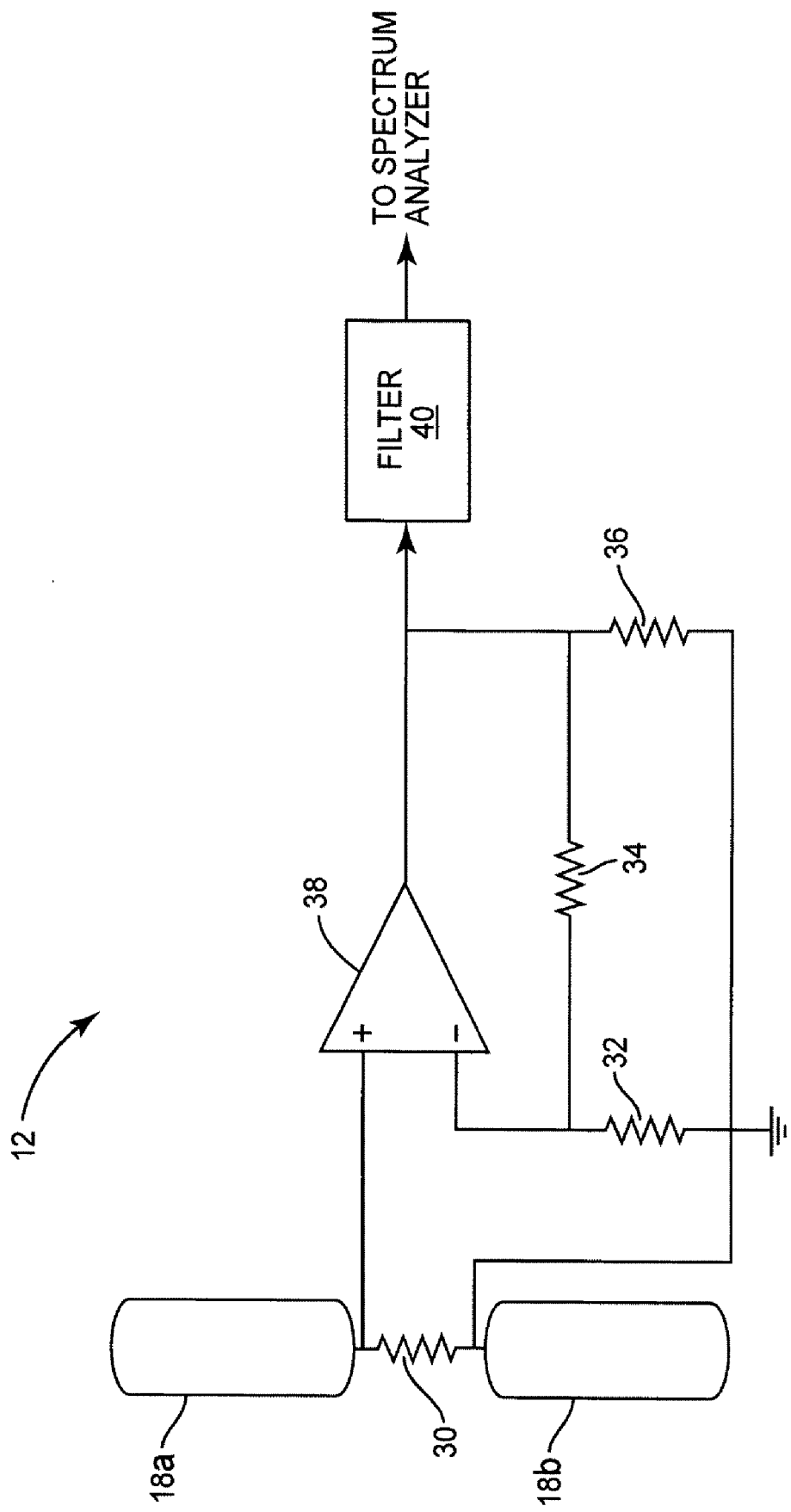
FIG. 3 illustrates the internal circuitry of an antenna configured to detect an electrical sinoatrial signal according to one embodiment of the present invention.

FIG. 3 illustrates the sensor 12 is more detail. As shown in FIG. 3, the sensing circuit in sensor 12 includes a plurality of resistors 30, 32, 34, 36, amplifier 38, and filter 40. Input resistor 30 connects the first conductive element 18a and the second conductive element 18b to the positive (+) input of the amplifier 38. Input resistor 30 is selected such that it provides a relatively high impedance to prevent loading of the weak ELF signals. In one embodiment, load resistor 30 may have a resistance greater than 100 MΩ and more preferably greater than 200 MΩ. Amplifier 38 increases the amplitude of the electrical sinoatrial signal. In a preferred embodiment, amplifier 38 is a low noise JFET operational amplifier, such as TL062 or LT1169. Resistors 32, 34, and 36 are coupled to the negative (−) output of amplifier 38 to properly bias amplifier 38.

Filter 40 is coupled to the output of amplifier 38 and removes 60 hertz frequency interference generated by electrical power lines in the United States, and thus prevents the interference from electrical power lines from saturating the signal. In another embodiment, filter 40 may remove 50 hertz frequency interference generated by electrical powers in other parts of the world, such as Europe. This allows spectrum analyzer 14 to accurately measure the ELF resonance produced by organs and limbs, which are significantly weaker than those produced by the electrical power lines. In a preferred embodiment, filter 40 is a 110 decibel notch filter.

Spectrum analyzer 14 is coupled to filter 40 of sensor 12 and transforms the acquired electrical sinoatrial signal from the time domain to the frequency domain. Spectrum analyzer 14 may comprise a processor or a computer executing spectrum analyzer software, such as fast Fourier transform. As discussed above, examination of human line spectra reveals a pattern of spectra peaks observed in the 0.1 to 40 hertz electromagnetic spectrum. Thus, the spectrum analyzer 14 is configured to output a frequency spectrum in the 0.1 and 40 hertz range. Accordingly, the width of the fast Fourier transform bin should be approximately 0.1 hertz to measure the bandwidth of the spectra peaks. In general, a range of 0 to −40 decibels will display human resonance.

Figure 4:
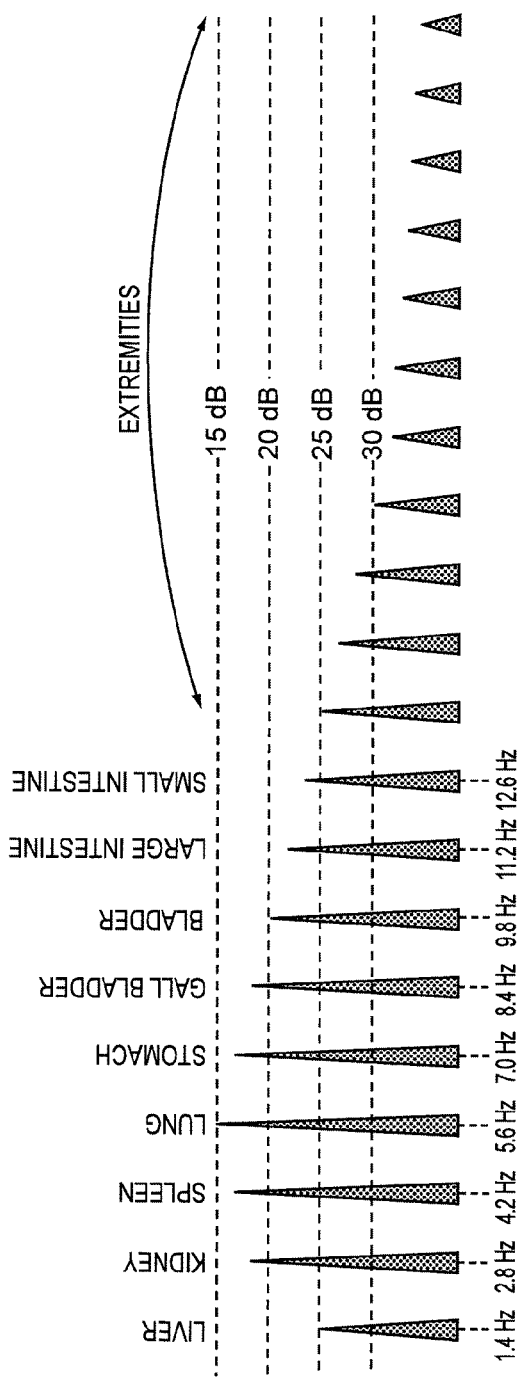
FIG. 4 is diagram of a normal frequency spectrum for a healthy person.

A healthy human exhibits 20 peaks, or frequency components, in the frequency spectrum between 0.1 and 40 hertz of the electrical sinoatrial signal. As shown in FIG. 4, each frequency component in the frequency spectrum corresponds to a particular organ or limb, such as arms and legs, in the human body. The lowest frequency spectra peak corresponds to the liver, the second peak corresponds to the kidney, the third peak corresponds to the spleen, followed by lung, stomach, gall bladder, bladder, large intestine, and small intestine resonance. The remaining peaks correspond to the arms, legs, and extra meridians.

Healthy cells in organs resonate at a specific frequency. Diseased cells in an organ alter the cells impedance, which decreases the organ's resonant properties. As the impedance of cells in an organ increases, the organ experiences decreasing resonance, which diminishes the capability of the sinoatrial node of oscillating at that frequency. Thus, if the impedance of an organ increases, the amplitude of the frequency associated with the organ decreases.

The diagnostic unit 16 analyzes the spectrum generated by the spectrum analyzer 14 to determine the condition of the organs or limbs of the human body. In particular, the amplitudes, bandwidth, and/or quality factor (Q) of the frequency components indicate health or illness associated with a specific organ or limb. In one embodiment, diagnostic unit 16 comprises computer software that compares the bandwidth, amplitude, and/or Q of each spectra peak to a standardized normal spectrum, as shown in FIG. 4, to determine the relative condition of the organs and limbs in the body.

The Q of a frequency component compares the frequency at which a system oscillates to the rate at which the system dissipates energy. Thus, a frequency component having a high Q indicates a low rate of energy dissipation relative to the oscillation frequency. Accordingly, a frequency component having a high Q will have narrower bandwidth than a frequency component having a low Q. A healthy organ is characterized by a frequency component having a high Q (narrow bandwidth). Disease in an organ decreases the ELF resonance of that organ, and thus, an unhealthy organ is characterized by a frequency component having a low Q (wide bandwidth). Generally, the Q of the spectra peak associated with a diseased organ decreases as the disease progresses.

The amplitude of the spectra peak quantifies energy exchange between the sinoatrial node and an organ. The highest peak in the human resonance frequency spectrum, is the body's natural resonant frequency and typically exhibits an amplitude of approximately 30 decibels above the noise floor. Each preceding and subsequent peak exhibits in a natural roll-off with decreased amplitudes. The lowest frequency peak exhibits an amplitude of only a few decibels above the noise floor. A spectra peak having a lower than normal amplitude indicates that the impedance transmission path between the organ and the sinoatrial node has increased. Increased impedance prevents the heart from generating sufficient energy required by the organ. Accordingly, an organ associated with a spectra peak having a low amplitude will become diseased if the impedance transmission path between the organ and the sinoatrial node does not return to normal.

In one embodiment, the highest peak in the frequency spectrum can be used to diagnose and treat depression. In experimental testing, individuals experiencing the recent death of a relative exhibited very low amplitudes associated with the natural resonant frequency. However, after several months, the amplitudes of these peaks returned to normal levels. Physicians can observe the amplitude of the highest peak to determine whether an individual should be treated with antidepressants or whether an existing antidepressant treatment is effective.

Figure 5:
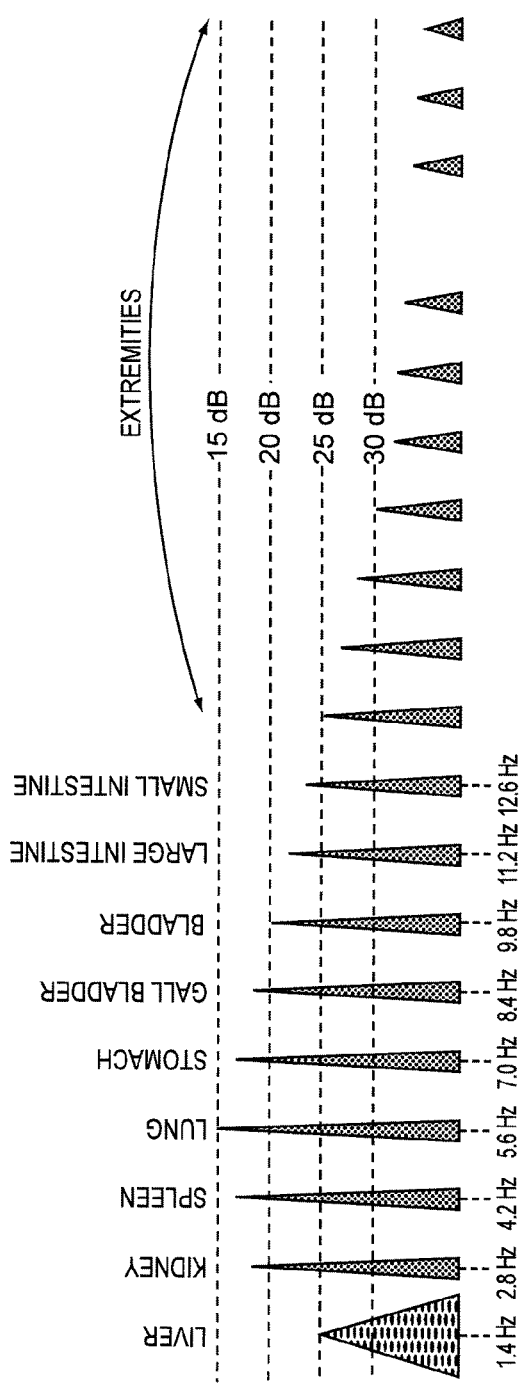
FIG. 5 illustrates an example of a frequency spectrum of an individual having a diseased liver and an amputated leg.

FIG. 5 illustrates a frequency spectrum of an individual with a diseased liver and an amputated leg. The peak associated with the liver, which has the lowest frequency pulse at 1.4 hertz, has a relatively normal amplitude and thus is receiving adequate energy from the heart. However, the bandwidth of the peak associated with the liver is relatively wide which indicates that the impedance transmission path between the liver and the sinoatrial node has increased. Thus, the liver is not receiving sufficient energy from the heart and may be diseased. The impedance of the diseased organ changes so that the organ's cells no longer resonate at 1.4 hertz. In addition, the missing spectra peak at 27 hertz reflects an amputated leg. That is, no energy is transferred between the sinoatrial node and the missing leg.

Figure 6:
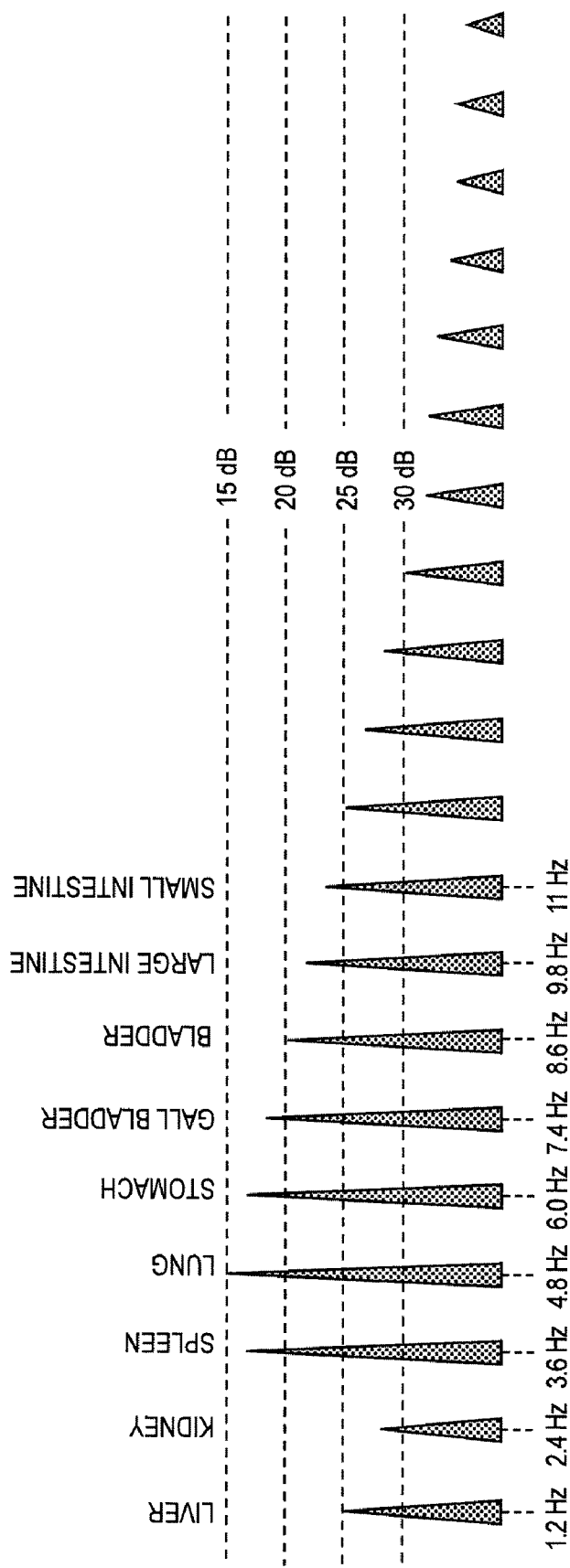
FIG. 6 illustrates an example of a frequency spectrum of an individual having a diseased kidney.

FIG. 6 illustrates a frequency spectrum of an individual with a diseased kidney. The second peak associated with the kidney is very low. Thus, little to no energy is transferred between the sinoatrial node and the kidney.

Figure 7:
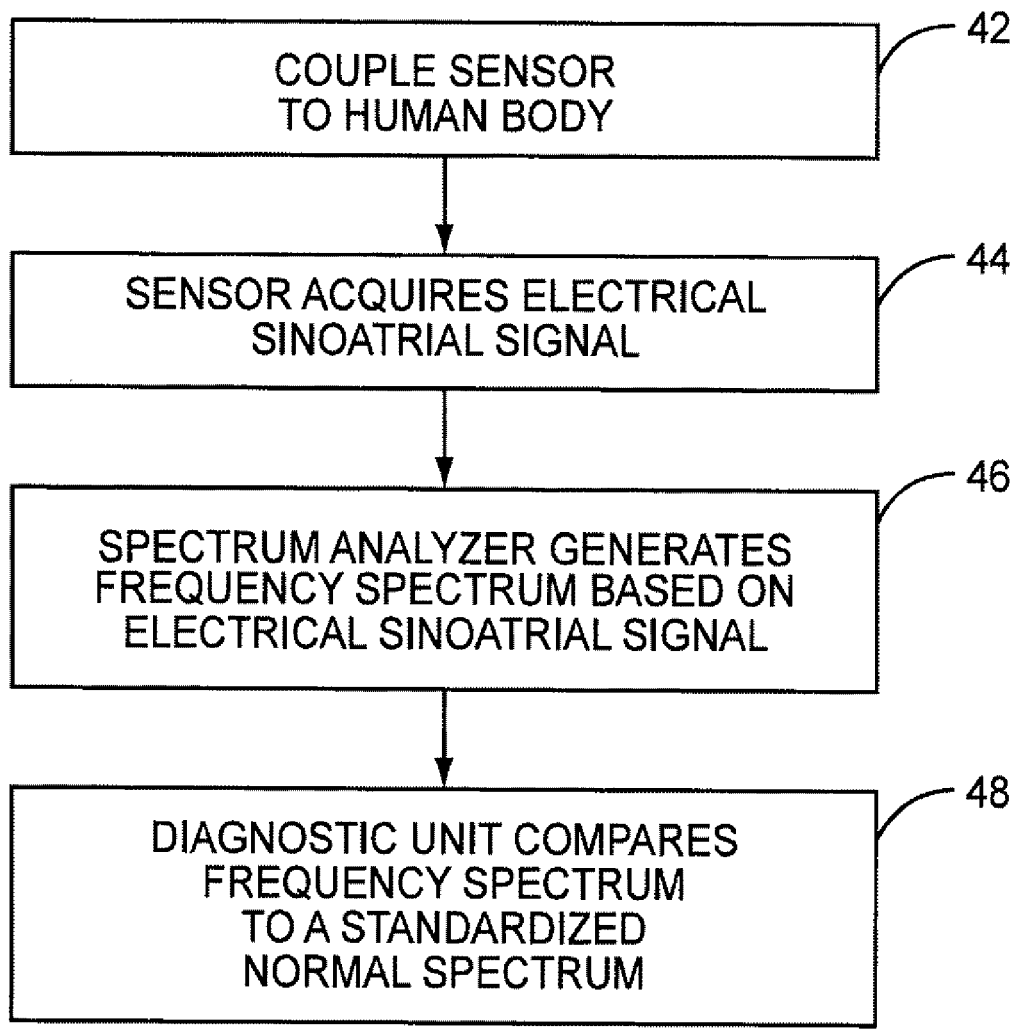
FIG. 7 is a flow diagram illustrating a method of performing one embodiment of the present invention.

FIG. 7 illustrates a method for diagnosing diseases of the organs according to one embodiment of the present invention. As shown in FIG. 7, an ELF sensor 12 is capacitatively coupled to a human body to acquire the electrical sinoatrial signal (block 42). Sensor 12 may be capacitatively coupled to a human body in several different ways. For example, sensor 12 may be laid on a person's chest, shoulders, waist, legs, or arms. In a preferred embodiment, a person can hold sensor 12 with a hand on each conductive element 18a, 18b. Once sensor 12 is coupled to a human, sensor 12 acquires the electrical sinoatrial signal (block 44). The acquired signal is input to spectrum analyzer 14, which generates a frequency spectrum based on the acquired electrical sinoatrial signal (block 46). Generally, spectrum analyzer 14 performs a fast Fourier transform to convert the electrical sinoatrial signal from the time domain to the frequency domain to generate the frequency spectrum. After the frequency spectrum is generated, diagnostic unit 16 compares the acquired frequency spectrum with a standardized normal spectrum associated with healthy organs (block 48). As discussed above, the amplitude, bandwidth, and/or Q of the peaks in the acquired frequency spectrum are analyzed to determine the condition of the organs and limbs of the body.

The frequency spectrum generated by the electrical sinoatrial signal also indicates the level of conscious and subconscious stress in the body. Stress causes a change in the bodies' capacitance. This change alters the frequencies of electromagnetic energy transferred to the organs and limbs by the sinoatrial node. Thus, the level of stress experienced by an individual increases or decreases the separation between frequency components in the frequency spectrum. Sustained deprivation of an organ's or limb's normal frequency by the sinoatrial node promotes disease in the organ or limb. Observing the frequency spectrum allows a physician to diagnose and treat individuals having high levels of stress before organs or limbs become diseased.

Conscious stress is measured by the separation between the frequency components in the 12 to 40 hertz range. Generally, the separation between frequency components ranges between 0.5 to 2 hertz. A human experiencing a higher level of conscious stress will exhibit an increased separation between frequency components, while an individual having little to no stress will exhibit a much smaller separation between frequency components. Thus, the frequency components associated with conscious stress can be monitored to determine the effect of meditation, relaxation, television, and music on the mind and body.

In one embodiment, the frequency spectrum can be used to diagnose Attention Deficit Hyperactivity Disorder (ADHD). Symptoms of ADHD include short attention span, hyperactivity, and impulsivity. Thus, an individual suffering from ADHD will exhibit frequency components associated with conscious stress that continuously oscillate approximately ±0.25 hertz. This continuous oscillation demonstrates that the individual has an increased difficulty focusing and maintaining attention on any one particular subject. By monitoring the frequency spectrum, physicians can easily diagnose and treat ADHD.

In another embodiment, the frequency spectrum can be used as a lie detector. For example, when an individual tells a lie, the individual experiences an increased conscious stress response. This increased conscious stress causes an increased separation between frequency components in the 12-40 hertz range.

Subconscious stress is measured by the separation between the frequency components in the 1 to 12 hertz range. The lowest frequency component in the frequency spectrum measures the magnitude of subconscious stress on the human body. A first frequency component below 1.2 hertz indicates a low subconscious stress level, while a first frequency component above 2 hertz indicates a high subconscious stress level and is associated with a health risk. Typically, an individual exhibits a low frequency component at approximately 1.4 hertz.

The present invention may, of course, be carried out in other ways than those specifically set forth herein without departing from essential characteristics of the invention. The present embodiments are to be considered in all respects as illustrative and not restrictive, and all changes coming within the meaning and equivalency range of the appended claims are intended to be embraced therein.

What is claimed is:

1. A method for detecting the presence of disease in organs comprising:
   detecting an electrical sinoatrial signal produced by a human heart by capacitatively coupling an antenna to a human body and detecting the electrical sinoatrial signal with an extremely low frequency antenna;
   processing the electrical sinoatrial signal to generate a frequency spectrum comprising a plurality of frequency components associated with different organs; and
   determining the condition of said organs by comparing said spectrum to a standardized normal spectrum associated with healthy organs.

2. The method of claim 1 wherein processing the electrical sinoatrial signal comprises converting the electrical sinoatrial signal from a time domain to a frequency domain using Fourier Transform.

3. The method of claim 2 wherein processing the electrical sinoatrial signal further comprises generating the frequency spectrum comprising the plurality of frequency components in a range between 0.1 and 40 hertz.

4. The method of claim 1 further comprising filtering the electrical sinoatrial signal to remove 60 hertz interference.

5. The method of claim 1 further comprising filtering the electrical sinoatrial signal to remove 50 hertz interference.

6. The method of claim 1 wherein determining the condition comprises analyzing an amplitude of at least one of the frequency components in the frequency spectrum.

7. The method of claim 1 wherein determining the condition comprises analyzing a bandwidth of at least one of the frequency components in the frequency spectrum.

8. The method of claim 1 wherein determining the condition comprises analyzing an amplitude and a bandwidth of at least one of the frequency components in the frequency spectrum.

9. A system for detecting the presence of disease in organs comprising:
   a sensor comprising an extremely low frequency antenna for sensing an electrical sinoatrial signal produced by a human heart;
   a spectrum analyzer for processing said electrical sinoatrial signal and generating a frequency spectrum based on said electrical sinoatrial signal, said frequency spectrum comprising a plurality of frequency components associated with different organs; and
   a diagnostic unit for determining the condition of said organs by comparing said spectrum to a standardized normal spectrum associated with healthy organs.

10. The system of claim 9 wherein the antenna comprises a first conductive element separated from a second conductive element and configured to be capacitatively coupled to a human body.

11. The system of claim 9 wherein the spectrum analyzer comprises a Fourier Transform device for converting the electrical sinoatrial signal from a time domain to a frequency domain.

12. The system of claim 11 wherein the Fourier Transform device generates the frequency spectrum comprising the plurality of frequency components in a range between 0.1 and 40 hertz.

13. The system of claim 9 further comprising a filter for removing 60 hertz interference.

14. The system of claim 9 further comprising a filter for removing 50 hertz interference.

15. The system of claim 9 wherein the frequency components in the spectrum have amplitudes characterizing the health of different organs.

16. The system of claim 9 wherein the frequency components in the spectrum have bandwidths characterizing the health of different organs.

17. A method for measuring stress in the human body comprising:
   detecting an electrical sinoatrial signal produced by a human heart by capacitatively coupling an antenna to a human body and detecting the electrical sinoatrial signal with an extremely low frequency antenna;
   processing the electrical sinoatrial signal to generate a frequency spectrum comprising a plurality of frequency components; and
   determining an amount of stress experienced by the human body by comparing said spectrum to a standardized normal spectrum associated with a human body experiencing very low or no stress.

18. The method of claim 17 wherein determining the amount of stress comprises analyzing a separation between the frequency components in the frequency spectrum.

* * * * *